(12) United States Patent
Yu et al.

(10) Patent No.: US 10,092,191 B2
(45) Date of Patent: Oct. 9, 2018

(54) JOINT VISUALIZATION OF 3D RECONSTRUCTED PHOTOGRAPH AND INTERNAL MEDICAL SCAN

(71) Applicant: Siemens Healthcare GmbH, Erlangen (DE)

(72) Inventors: Daphne Yu, Yardley, PA (US); Klaus Engel, Nürnberg (DE)

(73) Assignee: Siemens Healthcare GmbH, Erlangen (DE)

( * ) Notice: Subject to any disclaimer, the term of this patent is extended or adjusted under 35 U.S.C. 154(b) by 62 days.

(21) Appl. No.: 14/598,333

(22) Filed: Jan. 16, 2015

(65) Prior Publication Data

US 2016/0206203 A1    Jul. 21, 2016

(51) Int. Cl.
| | |
|---|---|
| *A61B 5/00* | (2006.01) |
| *G06T 11/00* | (2006.01) |
| *A61B 6/00* | (2006.01) |
| *G06T 15/04* | (2011.01) |
| *G06T 15/08* | (2011.01) |
| *G06T 15/20* | (2011.01) |
| *A61B 5/055* | (2006.01) |
| *A61B 6/03* | (2006.01) |

(52) U.S. Cl.
CPC .......... *A61B 5/0077* (2013.01); *A61B 5/0035* (2013.01); *A61B 6/466* (2013.01); *A61B 6/5247* (2013.01); *G06T 11/008* (2013.01); *G06T 15/04* (2013.01); *G06T 15/08* (2013.01); *G06T 15/205* (2013.01); *A61B 5/055* (2013.01); *A61B 6/032* (2013.01); *A61B 6/037* (2013.01); *A61B 6/5205* (2013.01); *G06T 2215/16* (2013.01)

(58) Field of Classification Search
None
See application file for complete search history.

(56) References Cited

U.S. PATENT DOCUMENTS

| | | | | |
|---|---|---|---|---|
| 6,975,756 | B1 * | 12/2005 | Slabaugh | G06T 15/205 345/427 |
| 2001/0007593 | A1 * | 7/2001 | Oosawa | G06F 19/321 382/132 |
| 2004/0225222 | A1 | 11/2004 | Zeng et al. | |
| 2006/0056700 | A1 * | 3/2006 | Abiko | G06K 9/0002 382/190 |
| 2007/0229500 | A1 | 10/2007 | Engel et al. | |

(Continued)

FOREIGN PATENT DOCUMENTS

| | | |
|---|---|---|
| CN | 1802122 A | 7/2006 |
| CN | 1842294 A | 10/2006 |
| DE | 102011084444 A1 * | 4/2013 ............. A61B 6/102 |

OTHER PUBLICATIONS

Chinese Office Action dated Mar. 28, 2018 in corresponding Chinese application No. 201610025858.2.

*Primary Examiner* — Sumati Lefkowitz
*Assistant Examiner* — Jiangeng Sun

(57) ABSTRACT

Interior scan and exterior photos are jointly visualized in medical imaging. One or more cameras are mounted to the internal medical scanner, allowing a photograph to be taken while or in temporal proximity to when the internal region of the patient is scanned. An image associating the exterior photographs with the interior region of the patient is presented to assist in diagnosis. Due to the spatial and temporal proximity, the image may be a visualization formed by combining the photograph and interior scan data.

13 Claims, 2 Drawing Sheets

(56) References Cited

U.S. PATENT DOCUMENTS

| | | | |
|---|---|---|---|
| 2009/0163809 A1* | 6/2009 | Kane | A61B 90/36 600/443 |
| 2009/0189889 A1 | 7/2009 | Engel et al. | |
| 2010/0328311 A1* | 12/2010 | Lakshmanan | G06T 17/20 345/427 |
| 2011/0092813 A1 | 4/2011 | Cable et al. | |
| 2012/0106814 A1* | 5/2012 | Gleason | A61B 6/037 382/131 |
| 2013/0229411 A1* | 9/2013 | Choi | G06T 17/00 345/419 |
| 2014/0241599 A1 | 8/2014 | Chen et al. | |
| 2016/0163115 A1* | 6/2016 | Furst | G06T 19/20 433/29 |

* cited by examiner

JOINT VISUALIZATION OF 3D RECONSTRUCTED PHOTOGRAPH AND INTERNAL MEDICAL SCAN

BACKGROUND

The present embodiments relate to medical imaging. In medical imaging, the interior of a patient is scanned. Various approaches for the scan are possible, such as magnetic resonance (MR), computed tomography (CT), x-ray, fluoroscopy, ultrasound, positron emission tomography (PET), or single photon emission computed tomography (SPECT). The data resulting from the scan is used to generate an image of the interior of the patient. Three-dimensional (3D) visualization is a common practice to assess and record the internal conditions of patients. Such internal images may lack information about the surface condition of the patient. The surface condition may be helpful in patient assessment.

Topical representations of the patient surface are not typically recorded. Observations may be performed by the attending physicians and recorded as verbal or written descriptions. In rare cases, pictures of the patient may be taken with a handheld camera during general examination.

BRIEF SUMMARY

By way of introduction, the preferred embodiments described below include methods, systems, instructions, and computer readable media for joint visualization in medical imaging. One or more cameras are mounted to the internal medical scanner, allowing photographs to be taken while or in temporal proximity to when the internal region of the patient is scanned. An image or images associating the exterior photographs with the interior region of the patient are presented to assist in diagnosis. Due to the spatial and temporal proximity, the image may be a visualization formed by combining the photographs and interior scan data.

In a first aspect, a system is provided for joint visualization in medical imaging. A medical imaging system is configured to scan an internal region of a patient. The medical imaging system has a patient area in which a patient is positioned during the scan. One or more cameras are connected to the medical imaging system so that the cameras are oriented to capture the patient in the patient area in a photograph or photographs. A processor is configured to generate an image as a function of the photograph and scan data from the scan. A display is configured to display the image.

In a second aspect, a method is provided for joint visualization in medical imaging. A medical imaging scanner scans a patient. A photographic camera or cameras acquire a one or more photographic images of the patient in the medical imaging scanner. A processor reconstructs a first three-dimensional representation of an internal region of the patient from the scanning and a second three-dimensional representation of the patient from the photographic image or images. The processor registers the first and second three-dimensional representations and renders a jointly visualized image from the first and second-three-dimensional representations as registered. The jointly visualized image is displayed.

In a third aspect, a computer readable storage medium has stored therein data representing instructions executable by a programmed processor for joint visualization in medical imaging. The storage medium includes instructions for: forming a 3D polygonal surface with texture from photographs taken by a camera(s) mounted to a medical imaging scanner, the photographs being of a patient; reconstructing a volume with scan data from the medical imaging scanner, the volume including an internal portion of the patient; rendering an image as a function of the 3D polygonal surface, the texture, and the volume; and displaying the image.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Photorealistic joint visualization of 3D reconstructed patient photo and medical image scan is provided. One or more cameras are connected with the medical scanner. The camera(s) captures multiple photos of the patient from multiple view points while the patient is positioned for the medical image scan. The photos and medical image scan are used for generating an image with at least some locations representing the patient surface in a photorealistic way. Having a surface view of the patient may provide a more comprehensive image review of the patient and may improve realism of the image data.

Figure 1:
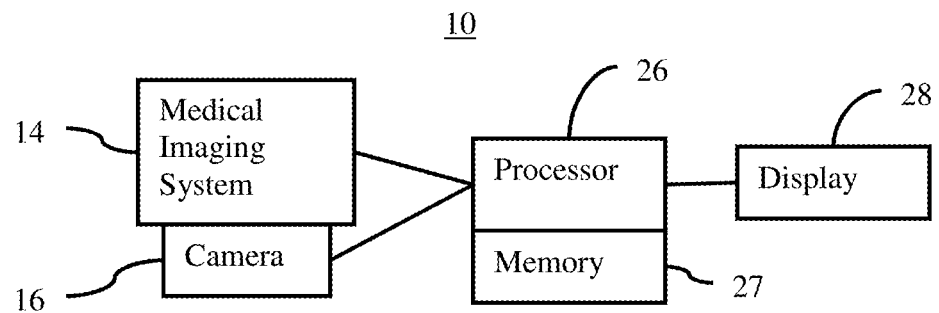
FIG. 1 is a block diagram of one embodiment of a system for jointly visualizing in medical imaging.

FIG. 1 shows a system 10 for joint visualization in medical imaging. The exterior is realistically visualized jointly with the interior of the patient.

The system 10 includes a medical imaging system 14, a camera 16, a processor 26, a memory 27, and a display 28. Additional, different, or fewer components may be provided. For example, a network or network connection is provided, such as for networking with a medical imaging network or data archival system. As another example, additional cameras or cameras of different types are provided. In another example, a user interface and corresponding input devices are provided. In yet another example, one or multiple light or flashlight sources connect to the gantry of the medical imaging system 14 or a connected elsewhere but directed towards the patient area. The light sources allow capture of the photos in desired lighting and/or simulate different lighting conditions for a lightstage approach.

The processor 26, memory 27, and display 28 are part of the medical imaging system 14. Alternatively, the processor 26, memory 27, and display 28 are part of an archival and/or image processing system, such as associated with a medical records database workstation or server. In other embodiments, the processor 26, memory 27, and display 28 are a personal computer, such as desktop or laptop, a workstation, a server, a network, or combinations thereof. The processor 26, memory 27, and display 28 may be parts of different systems, such as the memory 27 being in a picture archiving and communications system (PACS), the processor 26 being part of a workstation, and/or the display 28 being an imaging system 14 or radiological display.

The medical imaging system 14 is configured to scan an internal region of the patient. The surface or skin of the patient may also be scanned or may not be scanned. Any portion or extent of the patient may be scanned, such as a scan of an organ, torso, extremity, or full body. The scan acquires data representing the interior of the patient. The represented portion includes a volume or three-dimensional distribution of response from the patient.

Any medical imaging system 14 may be used. For example, the medical imaging system 14 is a CT, MR, ultrasound, x-ray, fluoroscopy, or emission tomography (i.e., functional imaging such as PET or SPECT) system. The medical imaging system 14 is any now known or later developed medical imaging system for scanning an interior of the patient.

Figure 2:
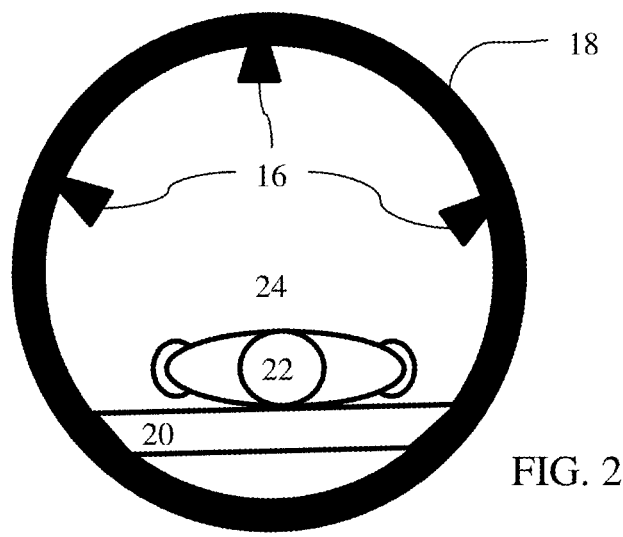
FIG. 2 illustrates an example embodiment of a patient being scanned.

FIG. 2 shows an example where the medical imaging system 14 includes a gantry or detector 18 that is positioned around the patient 22. The patient 22 is positioned on the bed 20 during the scan by the medical imaging system 14. The bed 20 is stationary. Alternatively, the bed 20 moves during the scan. The scan is performed with the patient 22 in the patient area 24 for scanning. The patient 22 rests on a bed 20 in a patient scan area 24 within, on, or adjacent to the gantry or detector 18. For example in CT, the gantry 18 supports a x-ray source and an opposing detector for rotating at least partially around the patient 22. For example in MR, a body coil as a detector 18 is positioned around the patient, but local coils may be used instead or as well. In yet another example, a ring of detectors 18 is positioned around the patient for PET. For a SPECT example, a planar gamma camera is connected with a gantry 18 for receiving emissions while positioned at different angles relative to the patient 22. Open or non-cylindrical structures may be used in other embodiments.

The medical imaging system 14 acquires signals from the internal region of the patient 22. The scan acquires data representing the internal region. For example, CT or MR data is acquired. The data represents tissue.

In FIG. 1, a single camera 16 is shown. In FIG. 2, three cameras 16 are shown. Any number of cameras 16 may be used. Each of the cameras 16 is of a same or different type.

A variety of camera type choices may be used. For instance, multiple standard digital still cameras 16 are provided. A charge coupled device (CCD), complementary metal oxide semiconductor (CMOS) or other digital camera with or without lenses may be used. Alternatively or additionally, a time-of-flight camera 16 is used. Laser or ultrasound is used to capture depth information of objects (e.g., the patient 22) with the camera 16. The distance to different locations in the field of view of the camera 16 is determined. As a result, a surface of the patient 22 in three-dimensions is determined.

Referring to FIG. 2, the camera 16 or cameras 16 are connected to the medical imaging system 14. For example, the cameras 16 connect to the gantry or detector 18. In other examples, the cameras 16 connect to a base or other structure of the medical imaging system 14 with one or more arms or other structures.

Any connection may be used, such as bolted, clamped, or latched. The connection is fixed, permanent, releasable, or moveable. In one embodiment, the cameras 16 are integrated within a housing on the gantry or detector 18. A window or opening is provided in the housing for capturing photos. In another embodiment, the cameras 16 connect on a joint or other fixture allowing automated or manual rotation and/or translation of the camera 16 relative to the medical imaging system 14.

The camera 16 is connected so that the camera 16 is oriented to capture the patient 22 in the patient area 24 in a photograph. The field of view of the camera 16 is set or selected to capture the exterior of the patient 22 over a scan extent of or greater extent that the medical imaging system 14. Alternatively, the camera 16 has a field of view less than the medical imaging scanner. The medical imaging system 14 acquires data representing parts of the patient that the cameras 16 cannot (e.g., interior and/or side against the bed 20). The extent of the field of view is along the surface of the patient axially and/or side-to-side. The field of view is approximately (e.g., within 20%) the same for the camera 16 or cameras 16 together and the medical imaging system 14, but may be different.

The cameras 16 capture the patient 22 while lying on the bed 20 for scanning. The bed 20 blocks camera-based capture of photos of the patient 22 against the bed 20. Alternatively, the bed 20 is transparent, allowing one or more cameras 16 to capture the patient 22 against the bed 20.

Where multiple cameras 16 are used, different cameras 16 may capture different parts or views of the overall field of view of the cameras 16. Based on the locations of the cameras 16, the cameras 16 may be oriented differently to capture different, but overlapping fields of view that in total represent the photographic field of view. The cameras 16 are at different angles relative to the patient 22 to photograph the patient 22 from different directions (see FIG. 2). A series of digital photos are acquired around the patient 22 to gather the surface view of the patient 22 from multiple surrounding angles. Alternatively, the cameras 16 are oriented to have overlapping similar fields of view, each capturing most (e.g., 80%) of the same field of view.

In the case of the digital still cameras 16, only a color or black and white representation of the surface is acquired. A photograph is acquired by the camera 16. The term photos or photographs include one or more frames from a sequence of photographs as videos or variations of extended photographs, such as photographs with depth information. For time-of-flight cameras 16, the depth between surfaces, including the patient surface, to the camera 16 is also acquired as an additional depth map. Each photo or map is a two-dimensional array of information. The depth map represents different depths distributed over the two-dimensional field of view.

One, more, or none of the cameras 16 may measure the light. For example, light arrays or other lighting is used to illuminate the patient. The light levels at different locations, such as on the surface of the patient are captured. The light locations and/or intensity may be measured. The camera 16 may measure the light level separately from capturing a photo. Alternatively, a captured photo may be processed to determine the light levels or locations and intensity of different light sources. Alternatively, the locations and intensity of different light sources is known as the lights are integrated with the medical imaging system 14. In yet other embodiments, separate sensors than the cameras 16 are used to measure the lighting level, lighting source locations, and/or light intensity. In yet other embodiments, the actual lighting conditions are not measured.

Referring to FIG. 1, the processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for rendering an image from data. The processor 26 is a single device or multiple devices operating in serial, parallel, or separately. The processor 26 may be a main processor of a computer, such as a laptop or desktop computer, or may be a processor for handling some tasks in a larger system, such as in an imaging system. The processor 26 is configured by hardware, firmware, and/or software.

The processor 26 is configured to trigger acquisition by the camera 16. A control line or wireless communication path extends from the processor 26 to the camera 16. The photograph acquisition is triggered by the processor 26 in synchronization with the scan. For example, the photograph is triggered to occur during the scan by the medical imaging system 14. Alternatively or additionally, the photograph is triggered to occur just prior to, just after, or in a break in the scanning by the medical imaging system 14. For example, the photograph is acquired within 1 second of the start or stop of scanning. By acquiring the photograph close in time with the scan, patient movement is limited or avoided. In alternative embodiments, other triggers are used (e.g., weight sensor on the bed) and/or the photograph is acquired a greater time before or after the scan.

The processor 26 also triggers the medical imaging system 14 to scan or receives a timing pulse indicated that the medical imaging system 14 is going to, has started, or has finished a scan. Alternatively, a separate trigger device is provided. The separate trigger device triggers the camera 16 and/or medical imaging system 14 to operate in synchronization.

After data acquisition, one or more photographs representing an exterior of the patient and one or more volumes (e.g., data sets representing locations distributed in three dimensions) representing at least an interior portion of the patient are provided. The data is stored in the memory 27, but separate storage may be used.

The processor 26 independently reconstructs three-dimensional representations of the patient from the scan and the photograph or photographs. The patient is three-dimensional. The scan data and the photograph represent the three-dimensional patient.

To reconstruct from the photographs, the processor 26 implements any now known or later developed reconstruction process to reconstruct a three-dimensional patient surface. A 3D model reconstruction algorithm creates a 3D polygonal surface and textures from the photograph or photographs. Using lighting variation, gradients, or comparisons from photographs at different angles, the processor 26 determines the surface of the patient in three dimensions. A photograph of a projected grid onto the patient 22 may be used to determine the surface in three-dimensions. Alternatively or additionally, the depth information from time-of-flight or other depth map is used.

Any mesh may be used. For example, the polygonal surface is a mesh of triangles. Any texturing may be used. For example, the photograph pixel values are used as textures for the polygons of the polygonal surface. The resulting polygonal surface in three dimensions and textures are a reconstruction of the surface of the patient in 3D. In alternative embodiments, other reconstruction representations may be used, such as other surfaces or a volume representation (e.g., fitting a three-dimensional model or shape).

The photographs may include representation of the bed, other part of the medical imaging system 14, and/or other background. To avoid or limit the background contribution to reconstructing the 3D surface of the patient, the background is removed or reduced. For example, a photograph or photographs of the patient area 24 are taken with the patient being absent. This photograph or photographs represent the background. By subtracting this or these photographs from the photograph or photographs of the patient 22, the background is removed or limited. Since the cameras capture the patient bed field of view, a set of background images without any patient may be used as a reference image model to automatically subtract out the background. The results of the background subtraction are used for reconstructing the 3D surface of the patient and generating a resulting image of the patient.

In alternative embodiments, imaging processing is used to remove the background. Since the cameras 16 are mounted on or around the scanner at approximately known locations, the field of view of the cameras 16 are known. Using this spatial information, background may be masked out. Imaging processing may be used to find colors or other indicators of the patient so that background is removed. For time-of-flight cameras 16, the depth map profiles may be used to assist in detecting the background more accurately. Optionally, manual processing of the images may be performed to minimize inaccurate background detection or to find background location.

The scan data may be output as a 3D reconstruction or data representing a volume. Alternatively, the acquired scan data is reconstructed to represent the volume. For example, Fourier processing is applied to k-space data in MR to reconstruct the volume. As another example, computed tomography is used to reconstruct the volume (e.g., SPECT, or CT). In yet another example, data representing three dimensions in a scan format is interpolated to a regular or other grid, such as a Cartesian coordinate grid. Each datum is associated with a different volume location (voxel) in the patient volume and assigned a scalar intensity. Each volume location is the same size and shape within the dataset. Volume locations with different sizes, shapes, or numbers along a dimension may be included in a same dataset.

The medical signal as acquired by the medical imaging system 14 is reconstructed independently of the surface from the photographs. The photographic data is not used in the reconstruction of the scan data and vice versa. In alternative embodiments, the photographic data is used for reconstructing from the scan data (e.g., a surface prior used in computed tomography) or vice versa (e.g., a surface from the scan data used to identify the surface where textures are from the photograph).

The processor 26 spatially registers the surface from the photograph with the volume from the scan data. The reconstructed three-dimensional representations are spatially registered. The translation, rotation, and/or scale to transform one reconstruction to the other are determined.

In one embodiment, the magnification of the photographs and location of the camera 16 relative to the medical imaging system 14 are used to register. The field of view of the camera 16 is calibrated so that the spatial alignment is known.

In other embodiments, the data is compared to register since the patient may move (e.g., voluntary, heart, or breathing). The reconstructed 3D surface from the photographs is registered with the volume reconstruction from the scan data. A best fit approach may be used to register the surface in the volume. The reconstructed 3D surface is registered with the corresponding patient surface implicitly represented within the 3D medical image volume. Alternatively, the surface of the patient represented within the scan data volume is specifically located and registered with the 3D surface from the photograph. In most medical image modalities, the intensity of air is distinct from the patient and other materials. An intensity or gradient-based threshold is applied to identify the patient surface in the scan data for then registering.

Any registration techniques for registering surfaces together or fitting a surface in a volume may be used. Example techniques include surface matching techniques (e.g., minimizing differences between two surfaces), mutual information techniques, point based techniques (e.g., minimizing differences between points of meshes), feature-based techniques (e.g., identifying the same features on both surfaces and registering the features), or statistical techniques. In one embodiment, a similarity or correlation (e.g., sum of absolute differences) with the surfaces at different relative positions is calculated. The alignment with the greatest similarity (e.g., minimum sum or maximum correlation) indicates the registration.

The translation, rotation, and/or scale that best aligns the surfaces are determined by the processor 26. The result of the registration is a rigid transformation represented as a matrix. The coordinates of the different 3D representations may be aligned or transformed such that spatial locations in each set representing a same tissue have a same or determinable location.

For some medical scans requiring a longer time, the patient may move. To deal with patient movement, a non-rigid transform may be determined. Deformable registration identifies a deformation of the volume to the surface, surface to surface, or the surface to the volume.

The processor 26 is configured to generate an image as a function of the photograph and scan data. The image is a single representation of the patient using both types of data (e.g., rendered as one dataset or separately rendered and overlaid). Alternatively, the image includes two separate representations, one from the scan data and the other from the photograph displayed side-by-side or simultaneously. In other embodiments, more than one or more than two representations of the patients may be included in an image, such as a rendering using both photographic and scan data as well as a multi-planar reconstruction images from the scan data.

The processor 26 is configured to generate the image from rendering or other image generation. For example, an image is rendered from a combination of the photograph and scan data. The three-dimensional reconstructions are combined based on the registration or resulting transform. For voxels represented by photograph texture, the photograph texture is used. For other voxels, the scan data is used. Alternatively, summing, averaging, alpha blending, maximum selection, minimum selection or other process is used to combine or select per voxel. The combined data set is rendered as a three-dimensional representation. The processor 26 renders the image from the combined data set. Any volume rendering may be used.

In other embodiments, the processor 26 renders from the photograph data and the scan data separately and combines the renderings (e.g., side-by-side or overlay). The surface from the photograph is rendered using any texture-based rendering or surface rendering. The volume from the scan data is rendered using volume rendering (e.g., alpha blending), but surface rendering may be used. In one approach, the 3D surface from the photograph and the volume from the scan data may be rendered simultaneously using surface volume hybrid rendering, where the surface is rendered and mapped with the camera photo textures and simultaneously the medical scan is rendered using a volume rendering technique.

To avoid cosmetic artifacts along the patient surface between the 3D surface model and the implicit patient surface in the medical scan from partial volume effect, registration error and noise within the medical scan, the rendering along the viewing ray may terminate the rays based on the 3D surface model from the photographs. The spatial registration positions the 3D surface relative to the volume of the scan data. For rendering from the scan data, the voxels only after the first sample of the surface has been rendered are used. The ray termination may be performed by comparing the depth buffer.

In an alternative approach, the image is rendered with ray line termination for the scan data at voxels defined by the photograph surface using a space skipping hull. The 3D surface is used as an empty space skipping hull for ray tracing or path tracing. The ray starts or is initialized at the first intersection of the ray with the surface and ends with the last intersection of the ray with the surface.

The processor 26 generates the image with or without added shading. The same shading is applied to all parts of the image or at least all representations of the patient in the image. Alternatively, different shading is applied to different parts, such as one type of shading for the image or voxel locations of the internal region (i.e., from the scan data) and another type of shading for the image or voxel locations from the skin surface (i.e., from the photograph data). For example in photorealistic rendering, path tracing approaches may be applied. Bidirectional reflectance distribution function (BRDF) surface shading is applied to contribution to the image representing the outside or surface of the patient, and bidirectional scattering distribution function (BTDF) shading is applied to contribution to the image representing the internal region of the patient. Where light is measured, the BRDF may be modeled as in a lightstage approach using the measured light information. The measured lighting is used for shading in the rendering. Subsurface scattering may also be applied to provide more realistic lighting of the patient skin. The subsurface scattering may be computed using soft tissue information acquired by the medical imaging scanner 14 and/or may be approximated using a skin subsurface scattering estimation. BTDF information for the volume data may use a model of the human body providing different light interaction for different types of tissue.

The processor 26 generates the image using photograph and scan data. The image is output by transfer or loading into a display buffer.

The display 28 is configured to display the image. The display 28 is a monitor, LCD, projector, plasma display, CRT, printer, or other now known or later developed devise for outputting visual information. The display 28 is configured by receiving images, graphics, or other information from the processor 26, memory 27, medical imaging system 14, or camera 16.

The display 28 receives the image rendered from the two different reconstructions. The image is output to the user. The image includes both information from inside the patient as well as information for the surface of the patient. The information from the surface of the patient is photo-based, at least in part, so provides photorealism in the rendered image. The photographic information is available in temporal and/or spatial alignment with the scan information for the interior of the patient, providing more information for diagnosis.

In one embodiment, the image changes over time, such as due to user interaction. For example, a rendering of the surface of the patient is originally shown. This rendering is just from the photograph data, but may include or show part of the internal region of the patient from the scan data. As the user positions a clipping plane or planes, different parts of the patient volume are masked. The outer surface of the patient closer to the viewer may be removed. As a result, the rendering shows the internal region from the scan data and any external region from the photograph not clipped or that intersects the clipping plane. Any skin surface still represented after cropping is shown with the representation of the internal region. The effect is as if a 3D photorealistic view of the patient is presented, but when any clipping is applied, the internal portion of the patient is revealed with the medical scan showing the internal structures of the patient as acquired by the medical scanner.

In another embodiment, the skin surface is shown semi-transparently. The data from the photograph only partially obscures the scan data. The viewer sees the skin surface representation, but may view through the skin surface to see representation of the internal region of the patient. Other rendering and resulting image from both types of data may be provided.

The image may result from the processor 26 applying any transfer function and/or segmentation. Transfer functions are applied to the volume data and/or skin surface data to visualize different anatomical features inside and outside of the patient. Segmentation may be used to color, hide, reveal, highlight, or alter anatomical features and/or to apply different BTDF for different tissue. The surface data may be composited with the volume rendering in different ways, such as rendering the skin as a glass-like surface with the internal anatomy (e.g., bones or organs) being viewable.

The memory 27 is a graphics processing memory, video random access memory, random access memory, system memory, cache memory, hard drive, optical media, magnetic media, flash drive, buffer, database, combinations thereof, or other now known or later developed memory device for storing photographs, scan data or video information. The memory 27 is part of the medical imaging system 14, part of a computer associated with the processor 26, part of a database, part of another system, or a standalone device.

The memory 27 stores datasets of different three-dimensional representations (e.g., patient volume and surface). The photographs, medical scan data, combined data set, reconstructions, rendering, and/or images are stored. Any data used for imaging, such as light measurements, or data in beginning, intermediate, or final stages of processing are stored for access by the processor 26.

The memory 27 or other memory is a computer readable storage medium storing data representing instructions executable by the programmed processor 26 for jointly visualizing in medical imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Figure 3:
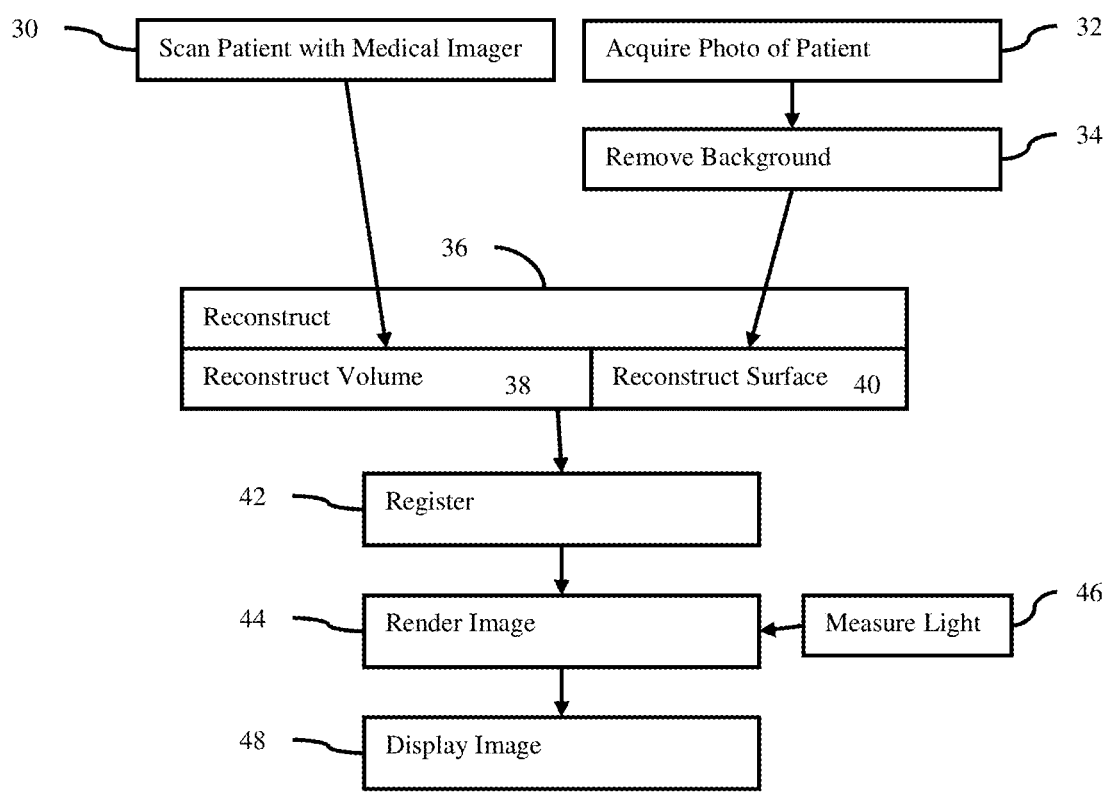
FIG. 3 is a flow chart diagram of one embodiment of a method for jointly visualizing in medical imaging.

FIG. 3 shows a method for joint visualization of the exterior and interior of a patient in medical imaging. The method is implemented by the system 10 of FIG. 1 or another system. For example, act 30 is performed by a medical scanner, acts 32 and 46 are performed with a camera and/or sensor, acts 34-44 are performed by a processor, computer, and/or the medical scanner, and act 48 is performed by a display. Any one or more of the acts may be performed by different devices.

The acts are performed in the order shown or other orders. For example, acts 30 and 32 are performed in either order or simultaneously. Acts 38 and 40 are performed in either order or simultaneously. Act 46 may be performed before or after act 32.

Additional, different, or fewer acts may be provided. For example, the display act 48 is not provided, but instead the image is saved or transferred. As another example, user input is provided for selecting display, controlling rendering, controlling registration, or other purposes.

In act 30, a patient is scanned with a medical imaging scanner. The interior of the patient is scanned, such as with MR, x-ray (e.g., CT), or emission tomography (e.g., PET or SPECT). The scan is performed in any format, such as detecting emissions along lines of response, acquiring k-space data at magnetic gradient defined locations, or acquiring projections through the patient with x-rays from different directions. As a result of the scan, data representing the interior of the patient is acquired.

In act 32, one or more photographic images of the patient are acquired with a camera. The camera is directed to the patient when and/or where the patient is being, has been, or is to be scanned by the medical imaging scanner. The camera may be connected with the medical imaging scanner or may be separate (not connected).

The patient is unclothed so that the photographic image is of the skin of the patient. Alternatively, the camera operates with millimeter waves or is a thermal camera to image the skin of the patient through clothing.

Photographs from different directions relative to the patient may be acquired. The camera moves to acquire from different angles and/or multiple cameras are used. The fields of view for the different images overlap or do not overlap.

The acquisition of acts 30 and 32 are synchronized to occur at a same time or within one second of each other. A medical scan may take seconds or minutes. During, just before, and/or just after the medical scan, the camera captures images. Any synchronization may be used, such as a trigger pulse or acquisition scheduling using a common or calibrated clock.

In act 34, the background is removed from the photographic images. Any removal may be used. Image processing detects the boundary of the patient, and data outside the boundary is removed. A photographic image of the space without the patient may be subtracted from the image of the patient to remove the background. Manual, automatic, or semi-automatic cropping may be used. Depth information may be used to identify background for removal.

The resulting photographic image after background removal represents just the patient. This resulting image is used to reconstruct a three-dimensional representation of the skin or outer surface of the patient.

In act 36, representations of the patient are reconstructed by a processor, such as a graphics processing unit. Photographic images and scan data from the scanner are available for reconstruction. Corresponding (e.g., two) reconstructions are performed to represent the patient three-dimensionally. Acts 38 and 40 are performed to create the corresponding reconstructions. Other reconstructions using the same or different data may be used.

In act 38, the processor reconstructs a volume representing, at least in part, an internal portion of the patient. Any reconstruction from the scan data may be used. The reconstruction determines scalar values for each of a plurality of voxels distributed in three dimensions. Alternatively, surface reconstruction is used, such as identifying and reconstruction three-dimensional surfaces for different organs.

In act 40, the exterior surface of the patient is reconstructed by the same or different processor. Any surface representation may be reconstructed, such as polygonal surface or other mesh. The mesh is populated with scalar values from and/or texture from the photographic image.

The representation of the exterior surface is 3D. Using depth mapping, image processing from photographs taken at different angles relative to the patient, deformations in a projected grid, or other process, the 3D exterior surface of the patient is reconstructed. A 3D polygonal surface with texture from a photograph taken by a camera mounted to a medical imaging scanner is formed.

In act 42, the reconstructed surface and volume are registered. The translation, rotation, and/or scale to best spatially fit the surface in the volume or the volume to the surface is determined. The processor registers the two three-dimensional representations. In one embodiment, an exterior surface of the patient represented in the reconstructed volume from scan data is identified. Thresholding or other image processing is applied to locate the exterior surface or a portion of the exterior surface represented by the scan data. The two surfaces are then registered. Using similarity measures, mutual information, cost function minimization, or other process, the transform relating the two representations to each other spatially is found.

The registration is rigid or affine. Alternatively, non-rigid or deformable registration may be used. The spatial relationship of voxels within a representation may be altered.

In act 44, an image is rendered from the three-dimensional representations. The processor or another processor renders an image using both scan and photographic data. The image is rendered as a function of the 3D polygonal surface, the texture from the photograph, and the scan volume.

Any rendering may be used, such as volume and/or surface rendering. The surface and volume combined may be volume rendered using projection. Alternatively, surfaces in the volume may be identified, and surface rendering of the photographic surface and the volume surfaces is performed. In other embodiments, surface rendering is used for the photographic surface, and volume rendering is used for the scan volume.

The three-dimensional representations, as registered, are combined for rendering. Alternatively, separate renderings are performed, and the resulting representations are aligned for overlay or side-by-side display based on the registration.

In one embodiment, the reconstructions are combined. A single representation of the patient is rendered from the combined data. Some pixels may be responsive to just the reconstructed surface from the photographs, and other pixels may be responsive to just the reconstructed volume from the scan data. Where the photograph data and/or scan data are semi-transparent, some pixels may be responsive to both types of data.

The rendering may use shading. The same or different shading is applied to different pixels. Where the pixel is more responsive (greater weighting) to scan data, one type of shading is used. Where the pixel is more responsive to photographic data, a different type of shading is used. Alternatively, the shading is applied to the voxel data as part of rendering, so voxels of photographic data are shaded in one way and voxels of scan data are shaded in another way before combination or rendering.

In one embodiment, the actual lighting in the room is used for shading. In act 46, the camera or other sensor measures the light to which the patient is subjected. Using the camera or other sensor, the shading may be adapted to the lighting of the room in which the patient is to be, has been or is being scanned. Alternatively, the local light information is acquired from a memory. The processor performs the shading in a way to model the actual lighting, such as setting a direction or directions of the light incident on the patient, setting an intensity of the light, or setting an amount of ambient light based on the measures.

In act 48, the rendered image is displayed by the processor on a display. The image represents the patient using both photographic and scan information. A photorealistic representation of the exterior of the patient is provided in combination with a medical scan representation of at least part of an interior of the patient. Due to clipping plane settings or other rendering settings, only the interior or only the exterior of the patient may be represented at other times.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for joint visualization in medical imaging, the system comprising:
   a medical imaging system configured to scan an internal region of a patient, the medical imaging system having a patient area in which a patient is positioned during the scan;
   a camera connected to the medical imaging system, the camera connected so that the camera is oriented to capture the patient in the patient area in a photograph;
   a processor configured to independently reconstruct a first three-dimensional representation of the patient from scan data of the scan and a second three-dimensional surface of the patient from the photograph and configured to render an image as a function of the first three-dimensional representation and the second three-dimensional surface with ray line termination for the scan data at voxels defined by the three-dimensional surface; and
   a display configured to display the image.

2. The system of claim 1 wherein the medical imaging system comprises a magnetic resonance, computed tomography, or an emission tomography system.

3. The system of claim 1 wherein the camera comprises a digital still camera.

4. The system of claim 1 further comprising at least a different camera connected to the medical imaging system oriented to capture the patient in the patient area in another photograph from a different angle relative to the patient than the photograph;
 wherein the processor is configured to reconstruct the three-dimensional patient surface from lighting variation, gradients, or comparison of the photograph relative to the other photograph.

5. The system of claim 1 wherein the camera comprises a time-of-flight camera configured to determine depths from different locations on a patient surface of the patient to the time-of-flight camera.

6. The system of claim 1 wherein the processor is configured to trigger acquisition of the photograph in synchronization with the scan with a temporal separation of acquiring the photograph and the scan of less than one second.

7. The system of claim 1 wherein the processor is configured to subtract a photograph of the patient area without the patient from the photograph of the patient, a result being used for generating the image.

8. The system of claim 1 wherein the processor is configured to spatially register a first surface of the first three-dimensional representation with the second three-dimensional surface.

9. The system of claim 1 wherein the processor is configured to render the image from a combination of the photograph and the scan data.

10. The system of claim 1 wherein the processor is configured to generate the image from a rendering of the photograph and a rendering of the scan data, the renderings being generated separately.

11. The system of claim 1 wherein the image corresponds to a clipping plane through a volume representing the patient, a skin surface at the clipping plane represented by the photograph and the internal region at the clipping plane represented by the scan data.

12. The system of claim 11 wherein the processor is configured to generate the image with a first type of shading for image locations of the internal region and a second, different type of shading for image locations of the skin surface.

13. The system of claim 1 wherein the processor is configured to render the image with a skin surface represented by the photograph shown semi-transparently in combination with at least a portion of the internal region represented by the scan data.

* * * * *